United States Patent
Bauer et al.

(10) Patent No.: US 9,587,206 B2
(45) Date of Patent: Mar. 7, 2017

(54) COMBINATION OF AN AMINO ALCOHOL, A FRAGRANCE AND A SILICIC ACID ESTER, AND THE USE OF SAME AS A PRO-FRAGRANCE

(71) Applicant: Henkel AG & Co. KGaA, Duesseldorf (DE)

(72) Inventors: Andreas Bauer, Kaarst (DE); Ursula Huchel, Cologne (DE); Andreas Gerigk, Erkelenz (DE); Marc Weyhe, Krefeld (DE); Thomas Gerke, Duesseldorf (DE); Hubert Smyrek, Krefeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/327,795

(22) Filed: Jul. 10, 2014

(65) Prior Publication Data
US 2014/0323375 A1   Oct. 30, 2014

Related U.S. Application Data

(63) Continuation of application No. PCT/EP2013/050245, filed on Jan. 9, 2013.

(30) Foreign Application Priority Data

Feb. 1, 2012   (DE) .................. 10 2012 201 422

(51) Int. Cl.
| | | |
|---|---|---|
| C11D 3/50 | (2006.01) | |
| A61K 8/41 | (2006.01) | |
| A61Q 13/00 | (2006.01) | |
| C11B 9/00 | (2006.01) | |
| A61K 8/58 | (2006.01) | |
| A61Q 19/00 | (2006.01) | |

(52) U.S. Cl.
CPC .................. *C11D 3/50* (2013.01); *A61K 8/41* (2013.01); *A61K 8/585* (2013.01); *A61Q 13/00* (2013.01); *A61Q 19/00* (2013.01); *C11B 9/0003* (2013.01); *C11B 9/0015* (2013.01); *C11D 3/507* (2013.01); *A61K 2800/10* (2013.01)

(58) Field of Classification Search
CPC .. C11D 3/50; C11D 3/507; A61K 8/41; A61K 8/25

See application file for complete search history.

(56) References Cited

U.S. PATENT DOCUMENTS

| | | | |
|---|---|---|---|
| 7,098,178 B2 | 8/2006 | Gerke et al. | |
| 8,466,294 B2 | 6/2013 | Huchel et al. | |
| 2004/0072704 A1* | 4/2004 | Gerke .................. | A61K 8/585 510/101 |
| 2010/0120657 A1 | 5/2010 | Lange et al. | |
| 2012/0309669 A1 | 12/2012 | Huchel et al. | |

FOREIGN PATENT DOCUMENTS

| | | |
|---|---|---|
| DE | 19841147 A1 | 3/2000 |
| WO | 2006/119283 A2 | 11/2006 |
| WO | 2008/134212 A1 | 11/2008 |
| WO | 2010/142479 A1 | 12/2010 |
| WO | 2010/142481 A1 | 12/2010 |
| WO | WO2010142481 * | 12/2010 |

OTHER PUBLICATIONS

PCT International Search Report (PCT/EP2013/050245) dated Mar. 26, 2013.

* cited by examiner

*Primary Examiner* — John Hardee
(74) *Attorney, Agent, or Firm* — Thomas G. Krivulka

(57) ABSTRACT

The invention relates to a composition of (a) a selected amino alcohol compound of general formula (I), (b) a scent aldehyde and/or scent ketone, and (c) a selected silicic acid ester, to the use of same as a pro-scent, as well as to washing and cleaning agents, fabric softeners and cosmetics which contain these. The invention also relates to a method for prolonging the perception of scent in such agents, and to a method for removing malodors by applying said composition.

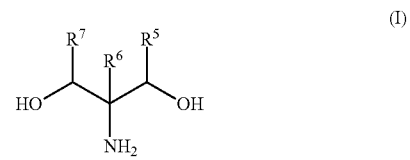

11 Claims, No Drawings

COMBINATION OF AN AMINO ALCOHOL, A FRAGRANCE AND A SILICIC ACID ESTER, AND THE USE OF SAME AS A PRO-FRAGRANCE

FIELD OF THE INVENTION

The present invention generally relates to a combination of an amino alcohol compound, a scent aldehyde and/or a scent ketone and a silicic acid ester. The invention also relates to its use as a pro-scent and washing and cleaning agents, fabric softeners and cosmetics that comprise same, to a method for prolonging the perception of scent in such agents as well as to a method for eliminating malodors.

BACKGROUND OF THE INVENTION

Besides the direct addition of scents to washing and cleaning agents, fabric softeners and cosmetics, the addition of so-called pro-scents was also proposed. In analogy to pro-drugs, the pro-scents represent a chemical derivative of a scent which for example reduces the volatility of the scent and enables a delayed release of the scent under ambient conditions. By derivatizing scents such as scent ketones, scent aldehydes or scent alcohols the vapor pressure of these compounds can be decreased. As the derivatization reaction is reversible, the chemically bound scent aldehyde, scent ketone or scent alcohol can be cleaved at the binding site under certain conditions, for example ambient conditions. In this way the fragrance or scent is released again which can lead to a prolonged perception of the scent.

In WO 2007/087977 A1 pro-scents are described that comprise a bound scent aldehyde and/or scent ketone in the form of a bicyclic oxazolidine.

DE 19841147 A1 discloses pro-scents in the form of silicic acid esters that release scent alcohols.

However, there is still a need to make available pro-scents that enable a prolonged perception of the scent with scent aldehydes, scent ketones and scent alcohols.

Accordingly, an object of the present application was to provide possibilities that enable a prolonged perception of the scent with scent aldehydes, scent ketones and scent alcohols.

Another object was to provide a possibility to eliminate malodors.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A combination of (a) an amino alcohol compound of the general Formula (I)

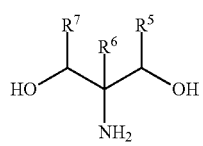

wherein $R^5$, $R^6$, $R^7$ independently of each other stand for H or a hydrocarbon group that can be acyclic or cyclic, substituted or unsubstituted, branched or unbranched as well as saturated or unsaturated, or mixtures of these compounds; (b) a scent aldehyde and/or scent ketone; and (c) a silicic acid ester of the general Formula (II):

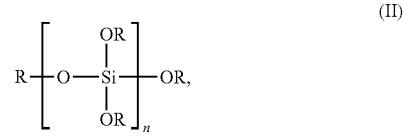

wherein all R, independently of each other, are selected from the group that comprises H, the linear or branched, saturated or unsaturated, substituted or unsubstituted $C_{1-6}$ hydrocarbon groups and the scent alcohol residue, and n assumes values in the range 2 to 100.

A washing or cleaning agent, fabric softener or cosmetics, comprising a combination of (a) an amino alcohol compound of the general Formula (I)

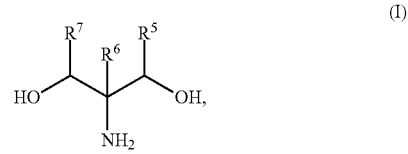

wherein $R^5$, $R^6$, $R^7$ independently of each other stand for H or a hydrocarbon group that can be acyclic or cyclic, substituted or unsubstituted, branched or unbranched as well as saturated or unsaturated, or mixtures of these compounds; (b) a scent aldehyde and/or scent ketone; and (c) a silicic acid ester of the general Formula (II):

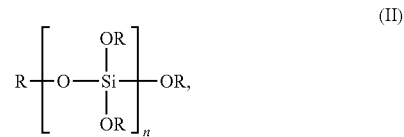

wherein all R, independently of each other, are selected from the group that comprises H, the linear or branched, saturated or unsaturated, substituted or unsubstituted $C_{1-6}$ hydrocarbon groups and the scent alcohol residue, and n assumes values in the range 2 to 100.

A method for eliminating malodors by adding a combination of (a) an amino alcohol compound of the general Formula (I)

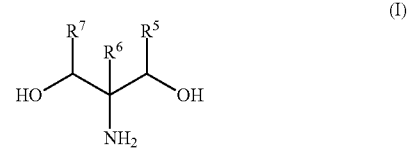

wherein $R^5$, $R^6$, $R^7$ independently of each other stand for H or a hydrocarbon group that can be acyclic or cyclic, substituted or unsubstituted, branched or unbranched as well as saturated or unsaturated, or mixtures of these compounds;

(b) a scent aldehyde and/or scent ketone; and (c) a silicic acid ester of the general Formula (II):

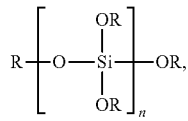
(II)

wherein all R, independently of each other, are selected from the group that comprises H, the linear or branched, saturated or unsaturated, substituted or unsubstituted $C_{1-6}$ hydrocarbon groups and the scent alcohol residue, and n assumes values in the range 2 to 100.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Surprisingly, it has now been found that the combination of
(a) an amino alcohol compound of the general Formula (I)

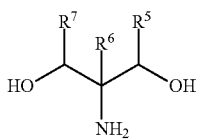
(I)

wherein $R^5$, $R^6$, $R^7$ independently of one another stand for H or a hydrocarbon residue that can be acyclic or cyclic, substituted or unsubstituted, branched or unbranched as well as saturated or unsaturated,
or mixtures of these compounds,
(b) a scent aldehyde and/or scent ketone and
(c) a silicic acid ester of the general Formula (II):

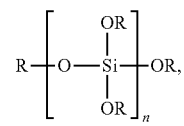
(II)

wherein all R, independently of each other, are selected from the group that comprises H, the linear or branched, saturated or unsaturated, substituted or unsubstituted $C_{1-6}$ hydrocarbon residues and the scent alcohol residue, and n assumes values in the range 2 to 100, affords a prolonged perception of the scent with scent aldehydes, scent ketones and scent alcohols and at the same time an improved elimination of malodors.

The scent aldehyde and/or the scent ketone preferably reacts at least partially under cyclization with the amino alcohol compound of the general Formula (I) to form a 1-aza-3,7-dioxabicyclo[3.3.0]octane compound of the general Formula (III)

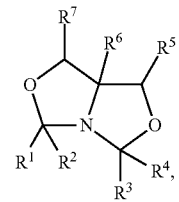
(III)

wherein $R^1$, $R^2$, $R^3$, $R^4$ independently of each other stand for groups that in a compound of the general Formula $R^1$—C(=O)—$R^2$ or $R^3$—C(=O)—$R^4$ form a scent aldehyde containing at least 6 carbon atoms or a scent ketone containing at least 6 carbon atoms.

Without wishing to be bound to this theory, it is assumed that the amino alcohol compound reacts with the scent aldehyde or the scent ketone to form bicyclic oxazolidine derivatives. Bicyclic oxazolidine derivatives of scent aldehydes and scent ketones lead to a decrease of the vapor pressure of the scent aldehydes and scent ketones and prolong the scent perception. In addition, the deposition of the bicyclic compounds on solid surfaces such as fabrics, skin or hard surfaces is improved.

The compounds of the general Formula (I) are derived from 2-amino-1,3-propane diol. By forming the bicyclic compounds it is possible to achieve a high degree of loading of the 2-amino-1,3-propane diol, such that the use of small amounts of the 2-amino-1,3-propane diol is required. Thus, a prolongation of the scent perception can already be achieved with lesser amounts of 2-amino-1,3-propane diol, leading inter alia to cost advantages and also avoiding the input of greater amounts of amino alcohol compound in agents, for example washing or cleaning agents, fabric softeners or cosmetics.

In particularly preferred compounds of the general Formula (III) $R^2$, $R^4$, $R^5$, $R^6$, $R^7$ mean hydrogen and $R^1$ and $R^3$ each mean a $C_{5-24}$ hydrocarbon residue.

The scent aldehydes and the scent ketones are particularly preferably selected from the jasmones, ionones, damascones and damascenones, menthone, carvone, iso-E-super, methylheptenone, melonal, cymal, ethyl vanillin, helional, hydroxycitronellal, koavone, methylnonylacetaldehyde, phenylacetaldehyde, undecylenaldehyde, 3-dodecen-1-al, alpha-n-amylcinnamaldehyde, benzaldehyde, 3-(4-tert-butylphenyl)-propanal, 2-methyl-3-(para-methoxyphenylpropanal), 2-methyl-4-(2,6,6-trimethyl-2(1)-cyclohexen-1-yl) butanal, 3-phenyl-2-propenal, cis/trans-3,7-dimethyl-2,6-octadien-1-al, 3,7-dimethyl-6-octen-1-al, [(3,7-dimethyl-6-octenyl)oxy]acetaldehyde, 4-isopropylbenzyaldehyde, 2,4-dimethyl-3-cyclohexene-1-carboxyaldehyde, 2-methyl-3-(isopropylphenyl)propanal, decylaldehyde, 2,6-dimethyl-5-heptenal, alpha-n-hexylcinnamaldehyde, 7-hydroxy-3,7-dimethyloctanal, undecenal, 2,4,6-trimethyl-3-cyclohexene-1-carboxaldehyde, 1-dodecanal, 2,4-dimethylcyclohexene-3-carboxaldehyde, 4-(4-hydroxy-4-methylpentyl)-3-cylohexene-1-carboxaldehyd, 2-methylundecanal, 2-methyldecanal, 1-nonanal, 1-octanal, 2,6,10-trimethyl-5,9-undecadienal, 2-methyl-3-(4-tert-butyl)propanal, dihydrocinnamaldehyde, 3,7-dimethyloctan-1-al, 1-undecanal, 10-undecen-1-al, 4-hydroxy-3-methoxybenzaldehyde, trans-4-decenal, 2,6-nonadienal, para-tolylacetaldehyde, 3,7-dimethyl-2-methylene-6-octenal, 2-methyloctanal, alpha-methyl-4-(1-methylethyl)benzeneacetaldehyde, 2-methyl-3-phenyl-2-propen-1-al, 3,5,5-trimethylhexanal, 3-propyl-bicyclo[2.2.1]hept-5-ene-2-carbaldehyde, 9-decenal, 3-methyl-5-phenyl-1-pentanal, methylnonylacetaldehyde, citral, 1-decanal, florhydral, 2,4-dimethyl-3-cyclohexene-1-carboxaldehyde, heliotropin and mixtures thereof.

These scent aldehydes and the scent ketones are particularly suitable for imparting a pleasant scent and/or a feeling of freshness to the agents.

It can also be preferred that the scent aldehyde and/or the scent ketone reacts at least partially under cyclization with the amino alcohol compound of the general Formula (I) to form a compound of the general Formula (IV)

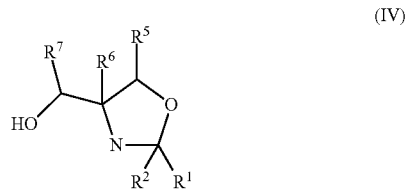

wherein $R^1$ and $R^2$ independently of one another stand for residues that in a compound of the general Formula $R^1$—C(=O)—$R^2$ form a scent aldehyde containing at least 6 carbon atoms or a scent ketone containing at least 6 carbon atoms.

It is also inventively possible that mixtures of single and twice blocked compounds are formed based on the 2-amino-1,3-propane diol derivatives.

In a preferred embodiment of the invention, a part of the R groups of the general Formula (II), preferably at least 5 mol % of the R groups, are selected from the group methyl, ethyl, n-propyl, isopropyl, n-butyl, isobutyl and tert-butyl.

Oligosilicic acid esters of lower alcohols are commercially available, wherein usually methanol, ethanol, n-propanol, isopropanol, n-butanol, isobutanol and tert-butanol were used for the esterification. The manufacture of oligosilicic acid esters that are incompletely transesterified with scent alcohols affords silicic acid ester mixtures, in which a part of the R residues is selected from the group methyl, ethyl, n-propyl, isopropyl, n-butyl, isobutyl and tert-butyl. Such compounds are preferred in the context of the present invention.

If incompletely transesterified oligosilicic acid esters are manufactured then the other R residues are preferably selected from the group of the scent alcohol residues.

Accordingly, at least 10 mol %, preferably at least 20 mol % and particularly preferably even more than 40 mol % of the R residues of the general Formula (II) are selected from the group consisting of the residues of the scent alcohols 10-undecen-1-ol, 2,6-dimethylheptan-2-ol, 2-methylbutanol, 2-methylpentanol, 2-phenoxyethanol, 2-phenylpropanol, 2-tert-butylcyclohexanol, 3,5,5-trimethylcyclohexanol, 3-hexanol, 3-methyl-5-phenylpentanol, 3-octanol, 3-phenylpropanol, 4-heptenol, 4-isopropylcyclohexanol, 4-tert-butylcyclohexanol, 6,8-dimethyl-2-nonanol, 6-nonen-1-ol, 9-decen-1-ol, alpha-methylbenzyl alcohol, alpha-terpineol, amyl salicylate, benzyl alcohol, benzyl salicylate, beta-terpineol, butyl salicylate, citronellol, cyclohexyl salicylate, decanol, dihydromyrcenol, dimethylbenzyl carbinol, dimethylheptanol, dimethyloctanol, ethyl salicylate, ethyl vanillin, eugenol, farnesol, geraniol, heptanol, hexyl salicylate, isobomeol, isoeugenol, isopulegol, linalool, menthol, myrtenol, n-hexanol, nerol, nonanol, octanol, p-menthan-7-ol, phenylethyl alcohol, phenol, phenyl salicylate, tetrahydrogeraniol, tetrahydrolinalool, thymol, trans-2-cis-6-nonadienol, trans-2-nonen-1-ol, trans-2-octenol, undecanol, vanillin, cinnamyl alcohol and mixtures thereof.

In a further preferred embodiment, n assumes values of 2 to 50, preferably from 2 to 20 and especially from 3 to 10, with particular preference for the values 4, 5, 6, 7 and 8.

As on economic grounds the starting compounds for manufacturing the silicic acid esters are preferably not pure substances, but rather industrial mixtures of oligosilicic acid esters of lower alcohols with different degrees of oligomerization, a distribution of the oligomerization degrees is also again found in the esters according to the invention which can correspond to the starting material or is modified by the reaction conditions.

The invention also relates to the use of the combination of (a) an amino alcohol compound of the general Formula (I), (b) a scent aldehyde and/or scent ketone and (c) a silicic acid ester of the general Formula (II) as the pro-scent. In this regard, it can be particularly preferred to employ the combination together with other scents.

The invention also relates to washing or cleaning agents, fabric softeners or cosmetics which comprise the combination of (a) an amino alcohol compound of the general Formula (I), (b) a scent aldehyde and/or scent ketone and (c) a silicic acid ester of the general Formula (II).

The invention further relates to a method for extending the perceived scent of washing or cleaning agents, fabric softeners or cosmetics or of hard surfaces treated with them, wherein the combination of (a) an amino alcohol compound of the general Formula (I), (b) a scent aldehyde and/or scent ketone and (c) a silicic acid ester of the general Formula (II) is added to the washing or cleaning agents, fabric softeners or cosmetics.

The invention further relates to a method for eliminating malodors by adding a combination of (a) an amino alcohol compound of the general Formula (I), (b) a scent aldehyde and/or scent ketone and (c) a silicic acid ester of the general Formula (II).

The term malodor is generally known to the person skilled in the art. In the context of this application, malodor includes all odors that are classified as unpleasant/bad by at least 7 persons in a group of ten persons. Examples of such malodors are the smell of sweat, fecal odors, mildew odor, bacterially produced malodor, fish odor, the smell of $C_1$ to $C_{15}$ fatty acids or the smell of damp washing stored for hours on end.

The elimination of malodors includes in particular the control and/or masking of malodors. The combination of (a) a selected amino alcohol compound, (b) a scent aldehyde and/or a scent ketone and (c) a selected silicic acid ester possesses synergistic properties when eliminating malodors, in particular for a period of a plurality of days.

The invention is intended to be described below in more detail inter alia by means of examples.

The combination comprises (a) a selected amino alcohol compound, (b) a scent aldehyde and/or a scent ketone and (c) a selected silicic acid ester as the essential ingredients.

The combination comprises an amino alcohol compound of the general Formula (I)

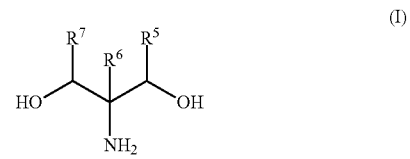

The amino alcohol compounds concern 2-amino-1,3-propane diols. $R^6$ can mean hydrogen or alkyl that can be substituted by one or two hydroxy groups and/or an amino group, wherein up to 8 non-neighboring —$CH_2$ groups can also be replaced by —O—. In this regard, alkyl residues are preferably $C_{1-24}$ alkyl residues, particularly preferably $C_{1-16}$ alkyl residues, in particular $C_{1-12}$ alkyl residues, specifically $C_{1-6}$ alkyl residues, for example $C_{1-3}$ alkyl residues. Here, the alkyl residues can be linear, branched or cyclic. They are preferably linear alkyl residues. They can concern mono or dihydroxyalkyl residues, which can also possess an amino group instead of or in addition to the hydroxy groups. The alkyl residues can furthermore be substituted or unsubstituted. In so far as the alkyl residues are interrupted by —O—, they preferably concern structural elements of the Formula —$CH_2$—$CH_2$—O— or —$CH_2$—$CH(CH_3)$—O—. These types of compound are easily obtained by alkoxylation of the corresponding hydroxy compounds.

Particularly preferred $R^6$ residues are methyl, ethyl, and hydroxymethyl residues.

$R^5$ and $R^7$ are hydrogen or a $C_{1-6}$ alkyl residue, preferably $C_{1-3}$ alkyl residues. $R^5$ and $R^7$ are particularly preferably hydrogen or a methyl or ethyl residue, especially hydrogen.

Preferred amino alcohol compounds are 2-amino-1,3-propane diol, 2-amino-2-hydroxymethyl-1,3-propane diol, 2-amino-2-methyl-1,3-propane diol, 2-amino-2-ethyl-1,3-propane diol and mixtures thereof.

The combination further comprises a scent aldehyde and/or a scent ketone. This means that the combination may comprise only one type of scent aldehyde or only one type of scent ketone. However, also included is that the combination can comprise one type of scent aldehyde and one type of scent ketone. Also included is that the combinations can comprise a plurality of types of scent aldehyde and a plurality of types of scent ketone. It is likewise possible that the combination comprises a plurality of types of scent aldehyde and one type of scent ketone or a plurality of types of scent aldehyde and a plurality of types of scent ketone. In another embodiment, the combination comprises a plurality of types of scent ketone and one type of scent aldehyde or a plurality of types of scent ketone and a plurality of types of scent aldehyde.

The scent ketones can include all ketones that can lend a desired scent or a sensation of freshness. Mixtures of different ketones can also be used. For example the ketone can be selected from the group consisting of buccoxime, isojasmone, methyl beta-naphthyl ketone, Moschus indanone, Tonalid/Moschus plus, alpha-damascone, beta-damascone, delta-damascone, iso-damascone, damascenone, damarose, methyl dihydrojasmonate, menthone, carvone, camphor, fenchone, alpha-ionenes, beta-ionone, dihydro-beta-ionone, gamma-methyl so-called ionone, fleuramone, dihydrojasmone, cis-jasmone, iso-E-Super, methyl cedrenyl ketone or methyl cedrylone, acetophenone, methylacetophenone, para-methoxyacetophenone, methyl beta-naphthyl ketone, benzylacetone, benzophenone, para-hydroxy-phenyl butanone, celery ketone or livescone, 6-isopropyldecahydro-2-naphtone, dimethyloctenone, frescomenthe, 4-(1-ethoxyvinyl)-3,3,5,5,-tetramethyl-cyclohexanone, methyl heptenone, 2-(2-(4-methyl-3-cyclohexen-1-yl)propyl)-cyclopentanone, 1-(p-menthen-6(2)-yl)-1-propanone, 4-(4-hydroxy-3-methoxyphenyl)-2-butanone, 2-acetyl-3,3-dimethyl-norbomane, 6,7-dihydro-1,1,2,3,3-pentamethyl-4 (5H)-indanone, 4-damascol, dulcinyl or cassion, gelsone, hexalone, isocyclemone E, methyl cyclocitrone, methyl lavender ketone, orivone, para-tert-butylcyclohexanone, verdone, delphone, muscone, neobutenone, plicatone, veloutone, 2,4,4,7-tetramethyl-oct-6-en-3-one, tetrameran, hedione and mixtures thereof. The ketones can preferably be selected from alpha damascone, delta damascone, iso damascone, carvone, gamma-methylionone, iso-E-super, 2,4,4,7-tetramethyl-oct-6-en-3-one, benzylacetone, beta damascone, damascenone, methyl dihydrojasmonate, methyl cedrylone, hedione and mixtures thereof.

Suitable scent aldehydes can be any aldehydes that produce, like the scent ketones, a desired scent or a sensation of freshness. Once again, they may be individual aldehydes or mixtures of aldehydes. Exemplary suitable aldehydes are melonal, triplal, ligustral, adoxal, anisaldehyde, cymal, ethylvanillin, florhydral, helional, heliotropine, hydroxycitronellal, koavone, laurinaldehyde, lyral, methylnonyl-acetaldehyde, p, t-bucinal, phenylacetaldehyde, undecylene aldehyde, vanillin, 2,6,10-trimethyl-9-andecenal, 3-dodecen-1-al, alpha-n-amylcinnamaldehyde, 4-methoxybenzaldehyde, benzaldehyde, 3-(4-tert-butylphenyl)-propanal, 2-methyl-3-(para-methoxyphenylpropanal), 2-methyl-4-(2, 6,6-trimethyl-2(1)-cyclohexen-1-yl)butanal, 3-phenyl-2-propenal, cis-/trans-3,7-dimethyl-2,6-octadien-1-al, 3,7-dimethyl-6-octen-1-al, [(3,7-dimethyl-6-octenyl)oxy] acetaldehyde, 4-isopropylbenzaldehyde, 1,2,3,4,5,6,7,8-octahydro-8,8-dimethyl-2-naphthaldehyde, 2,4-dimethyl-3-cyclohexen-1-carboxyaldehyde, 2-methyl-3-(isopropyl-phenyl)propanal, decyl aldehyde, 2,6-dimethyl-5-heptenal, 4-(tricyclo[5.2.1.0 (2,6)]-decylidene-8)-butanal, octahydro-4,7-methano-1H-indene carboxaldehyde, 3-ethoxy-4-hydroxybenzaldehyde, para-ethyl-alpha,alpha-dimethylhydrocinnamaldehyde, alpha-methyl-3,4-(methylenedioxy)-hydrocinnamaldehyde, 3,4-methylenedioxybenzaldehyde, alpha-n-hexylcinnamaldehyde, m-cymene-7-carboxaldehyde, alpha-methylphenylacetaldehyde, 7-hydroxy-3,7-dimethyloctanal, undecenal, 2,4,6-trimethyl-3-cyclohexene-1-carboxaldehyde, 4-(3) (4-methyl-3-pentenyl)-3-cyclohexene carboxaldehyde, 1-dodecanal, 2,4-dimethyl cyclohexene-3-carboxaldehyde, 4-(4-hydroxy-4-methylpentyl)-3-cyclohexene-1-carboxaldehyde, 7-methoxy-3,7-dimethyloctan-1-al, 2-methylundecanal, 2-methyldecanal, 1-nonanal, 1-octanal, 2,6,10-trimethyl-5,9-undecadienal, 2-methyl-3-(4-tertbutyl)propanal, dihydrocinnamaldehyde, 1-methyl-4-(4-methyl-3-pentenyl)-3-cyclohexene-1-carboxaldehyde, 5 or 6-methoxyhexahydro-4,7-methanoindane-1 or 2-carboxyaldehyde, 3,7-dimethyloctan-1-al, 1-undecanal, 10-undecen-1-al, 4-hydroxy-3-methoxybenzaldehyde, 1-methyl-3-(4-methylpentyl)-3-cyclohexene carboxyaldehyde, 7-hydroxy-3,7-dimethyl-octanal, trans-4-decenal, 2,6-nonadienal, para-tolyl-acetaldehyde, 4-methylphenylacetaldehyde, 2-methyl-4-(2, 6,6-trimethyl-1-cyclohexen-1-yl)-2-butenal, ortho-methoxycinnamaldehyde, 3,5,6-trimethyl-3-cyclohexene carboxaldehyde, 3,7-dimethyl-2-methylene-6-octenal, phenoxyacetaldehyde, 5,9-dimethyl-4,8-decadienal, peony aldehyde (6,1-dimethyl-3-oxa-5,9-undecadien-1-al), hexahydro-4,7-methanoindane-1-carboxaldehyde, 2-methyloctanal, alpha-methyl-4-(1-methylethyl) benzeneacetaldehyde, 6,6-dimethyl-2-norpinene-2-propionaldehyde, para-methyl-phenoxyacetaldehyde, 2-methyl-3-phenyl-2-propen-1-al, 3,5,5-trimethylhexanal, hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methylnonylacetaldehyde, 1-p-menthene-q-carboxaldehyde, citral or mixtures thereof, lilial citral, 1-decanal, florhydral, 2,4-dimethyl-3-cyclohexene-1-carboxaldehyde, preferred aldehydes can be selected from cis/trans-3,7-dimethyl-2,6-octadien-1-al, heliotropin, 2,4,6-trimethyl-3-cyclohexene-1-carboxaldehyde, 2,6-nonadienal, alpha-n- amylcinnamaldehyde, alpha-n-hexylcinnamaldehyde, p-tert-bucinal, lyral, cymal, methylnonylacetaldehyde, trans-2-nonenal, lilial, trans-2-nonenal and mixtures thereof.

As mentioned previously in the examples, the scent aldehydes and/or the scent ketones can have an aliphatic, cycloaliphatic, aromatic, ethylenically unsaturated structure or a combination of these structures. Additional heteroatoms or polycyclic structures can also be present. The structures can possess suitable substituents such as hydroxy or amino groups.

In addition, the listed scent aldehydes and/or the scent ketones have particularly good results in combatting and masking malodors.

As the third essential component, the combination comprises a silicic acid ester of the general Formula (II)

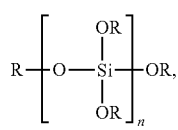

(II)

wherein all R, independently of each other, are selected from the group that comprises H, the linear or branched, saturated or unsaturated, substituted or unsubstituted $C_{1-6}$ hydrocarbon residues and the scent alcohol residues, and n assumes values in the range 2 to 100.

The cited compounds are produced by simple transesterification of oligosilicic acid esters of lower alcohols with scent alcohols, wherein both individual scent alcohols as well as mixtures of scent alcohols may be used. According to the reaction time and conditions, the lower alcohols are cleaved and the scent or biocidal alcohols are bonded, the alcohols along Si—O—Si chains being more easily exchanged than the terminal alcohols. The commercially available silicic acid esters are usually employed as the starting materials. In particular, the ethyl esters may be cited here. The transesterification reaction may be controlled solely by increasing the temperature and distilling off the readily volatile by-products; however, catalysts are preferably used for the transesterification. The catalysts used are typically Lewis acids, preferably aluminum tetraisopropylate, titanium tetraisopropylate, silicon tetrachloride or basic catalysts or even preparations, for example of aluminum oxide with potassium fluoride. The thus-formed oligomeric silicic acid esters then at least partially possess scent alcohol residues. However, the resulting esters normally also contain residues of lower alcohols. If small quantities of water or other hydrogen-acidic compounds are present during the production, then an exchange of alcohol residues also occurs against OH groups. Consequently, the mixtures of silicic acid esters according to the invention to some extent also usually comprise hydrogen as the residue R.

Oligosilicic acid esters of lower alcohols are commercially available, wherein usually methanol, ethanol, n-propanol, isopropanol, n-butanol, isobutanol and tert-butanol were used for the esterification. The synthesis of oligosilicic acid esters that are incompletely transesterified with scent alcohols affords silicic acid ester mixtures, in which a part of the R residues is selected from the group methyl, ethyl, n-propyl, isopropyl, n-butyl, isobutyl and tert-butyl.

If incompletely transesterified oligosilicic acid esters are manufactured then the other R residues are preferably selected from the group of the scent alcohol residues.

In the context of the present invention, the term "scent alcohols" is understood to mean scents, which possess free hydroxyl groups that are esterifiable, irrespective of how the molecule is further constructed. Thus, salicylic acid esters can also be used as scent alcohols. Preferred representatives of the large group of the scent alcohols can be cited, such that in the context of the present invention silicic acid esters are preferred, in which each R and R is selected independently of each other from the group of the residues of the following scent alcohols: 10-undecen-1-ol, 2,6-dimethylheptan-2-ol, 2-methylbutanol, 2-methylpentanol, 2-phenoxyethanol, 2-phenylpropanol, 2-tert-butylcyclohexanol, 3,5,5-trimethylcyclohexanol, 3-hexanol, 3-methyl-5-phenylpentanol, 3-octanol, 3-phenylpropanol, 4-heptenol, 4-isopropylcyclohexanol, 4-tert-butylcyclohexanol, 6,8-dimethyl-2-nonanol, 6-nonen-1-ol, 9-decen-1-ol, alpha-methylbenzyl alcohol, alpha-terpineol, amyl salicylate, benzyl alcohol, benzyl salicylate, beta-terpineol, butyl salicylate, citronellol, cyclohexyl salicylate, decanol, dihydromyrcenol, dimethylbenzyl carbinol, dimethylheptanol, dimethyloctanol, ethyl salicylate, ethyl vanillin, eugenol, farnesol, geraniol, heptanol, hexyl salicylate, isoborneol, isoeugenol, isopulegol, linalool, menthol, myrtenol, n-hexanol, nerol, nonanol, octanol, p-menthan-7-ol, phenylethyl alcohol, phenol, phenyl salicylate, tetrahydrogeraniol, tetrahydrolinalool, thymol, trans-2-cis-6-nonadienol, trans-2-nonen-1-ol, trans-2-octenol, undecanol, vanillin, cinnamyl alcohol and mixtures thereof.

The phenylethyl esters of silicic acid, geranyl esters of silicic acid, citronellyl esters of silicic acid, cinnamyl esters of silicic acid, hexenyl esters of silicic acid, nonadienyl esters of silicic acid, octenyl esters of silicic acid or mixtures of two or more of these esters of silicic acid are preferably employed.

The quantity of amino alcohol of the general Formula (I) in the combination is preferably 0.5 to 50 wt %, relative to the total quantity of the combination. The quantity of scent aldehyde and/or scent ketone in the combination is preferably 0.5 to 50 wt %, relative to the total quantity of the combination. The quantity of silicic acid ester of the general Formula (II) in the combination is preferably 0.5 to 50 wt %, relative to the total quantity of the combination.

The combination of (a) the selected amino alcohol compound, (b) scent aldehyde and/or scent ketone and (c) the selected silicic acid ester is preferably employed as the pro-scent. In this regard, the term "pro-scent" describes derivatives of scent aldehydes and scent ketones, which under ambient conditions release the original scent aldehydes and scent ketones. In this regard, ambient conditions are the typical ambient conditions in the human environment or the conditions encountered on human skin. Under ambient conditions the compounds of the general Formula (I) slowly decompose thereby reversing the production process and release the original scent aldehydes and/or scent ketones. The chemically bonded scent aldehydes and scent ketones are cleaved at the bonding site, thereby releasing the scents again.

Consequently, the use of the described combination as the pro-scent that preferably releases scent aldehydes and/or scent ketones as the scent is particularly preferred.

The disclosed combination can be used alone, for example as a perfume, but it is also possible to use mixtures of scents that only partly consist of the described combination.

In a preferred embodiment, a perfume comprises a combination of (a) an amino alcohol compound of the general Formula (I)

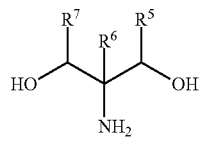

wherein $R^5$, $R^6$, $R^7$ independently of one another stand for H or a hydrocarbon residue that can be acyclic or cyclic, substituted or unsubstituted, branched or unbranched as well as saturated or unsaturated,
or mixtures of these compounds,
(b) a scent aldehyde or a scent ketone and
(c) a silicic acid ester of the general Formula (II):

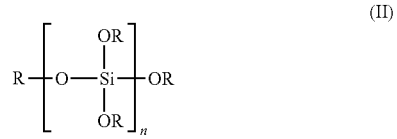

wherein all R, independently of each other, are selected from the group that comprises H, the linear or branched, saturated or unsaturated, substituted or unsubstituted $C_{1-6}$ hydrocarbon residues and the scent alcohol residue, and n assumes values in the range 2 to 100.

Thus, perfumes can be particularly employed that comprise 0.1 to 50 wt %, preferably 0.5 to 40 wt % and in particular maximum 30 wt % of the combination of (a) the selected amino alcohol compound, (b) scent aldehyde and/or scent ketone and (c) the selected silicic acid ester As a result of the splitting of the total perfume content of an agent, for example a washing or cleaning agent, into perfume that is present in the form of the described combination and perfume that was conventionally incorporated, a plurality of product characteristics can be realized, which are first made possible by the described combination of (a) the selected amino alcohol compound, (b) scent aldehyde and/or scent ketone and (c) the selected silicic acid ester.

In contrast, the scents that can be incorporated into the agents in a conventional manner are not subject to any limitations. Suitable scents or perfume oils that can be used include individual scent compounds of natural or synthetic origin, e.g. of the ester, ether, aldehyde, ketone, alcohol and hydrocarbon type. Scent compounds of the ester type are e.g. benzyl acetate, phenoxyethyl isobutyrate, p-tert-butylcyclohexyl acetate, linalyl acetate, dimethylbenzyl carbinyl acetate (DMBCA), phenylethyl acetate, benzyl acetate, ethylmethylphenyl glycinate, allylcyclohexyl propionate, styrallyl propionate, benzyl salicylate, cyclohexyl salicylate, floramate, melusate and jasmacyclate. The ethers include, for example, benzyl ethyl ether and ambroxan; the aldehydes include, for example, the linear alkanals containing 8 to 18 carbon atoms, citral, citronellal, citronellyloxyacetaldehyde, cyclamen aldehyde, lilial and bourgeonal; the ketones include, for example, the ionones, alpha-isomethyl ionone and methyl cedryl ketone; the alcohols include anethole, citronellol, eugenol, geraniol, linalool, phenylethyl alcohol and terpineol and the hydrocarbons include, in particular the terpenes, such as limonene and pinene. However, mixtures of various scents, which together produce an attractive fragrant note, are preferably used.

Perfume oils such as these may also contain natural mixtures of scents, as are obtainable from vegetal sources, for example pine, citrus, jasmine, patchouli, rose or ylang-ylang oil. Also suitable are muscatel sage oil, chamomile oil, clove oil, melissa oil, mint oil, cinnamon leaf oil, lime blossom oil, juniper berry oil, vetivert oil, olibanum oil, galbanum oil and laudanum oil as well as orange blossom oil, neroli oil, orange peel oil and sandalwood oil.

Other exemplary conventional oils that may be employed in the context of the present invention are die essential oils such as angelica root oil, aniseed oil, arnica blossom oil, basil oil, bay oil, champaca blossom oil, silver birch oil, silver birch cone oil, elemi oil, eucalyptus oil, fenchel oil, spruce needle oil, galbanum oil, geranium oil, ginger grass oil, guaiac wood oil, gurjun balm oil, helichrysum oil, ho-oil, ginger oil, iris oil, cajuput oil, calmus oil, camilla oil, camphor oil, kanaga oil, cardamom oil, cinnamon oil, pine needle oil, copaiba balsam oil, coriander oil, spearmint oil, caraway oil, cumin oil, lavender oil, lemon grass oil, lime oil, mandarin oil, melissa oil, musk grain oil, myrrh oil, clove oil, neroli oil, niaouli oil, olibanum oil, origanum oil, palmarosa oil, patchouli oil, perubalsam oil, petitgrain oil, pepper oil, peppermint oil, allspice oil, pine-oil, rose oil, rosemary oil, sandalwood oil, celery oil, spike oil, star anise oil, turpentine oil, thuja oil, thyme oil, verbena oil, vetivert oil, juniper berry oil, wormwood oil, wintergreen oil, ylang-ylang oil, ysop oil, cinnamon oil, cinnamon leaf oil, citronellol oil, lemon oil as well as cypress oil as well as ambrettolide, ambroxan, alpha-amylcinnamaldehyde, anethol, anisaldehyde, anise alcohol, anisole, anthranilic acid methyl ester, acetophenone, benzylacetone, benzaldehyde, benzoic acid ethyl ester, benzophenone, benzyl alcohol, benzyl acetate, benzyl benzoate, benzyl formate, benzyl valerate, borneol, bornyl acetate, Boisambrene forte, alpha-bromostyrene, n-decylaldehyde, n-dodecylaldehyde, eugenol, eugenol methyl ether, eucalyptol, farnesol, fenchone, fenchyl acetate, geranyl acetate, geranyl formate, heliotropine, heptyne carboxylic acid methyl ester, heptaldehyde, hydroquinone dimethyl ether, hydroxycinnamaldehyde, hydroxycinnamyl alcohol, indole, iron, isoeugenol, isoeugenol methyl ether, isosafrol, jasmone, camphor, carvacrol, carvone, p-cresol methyl ether, coumarin, p-methoxyacetophenone, methyl n-amyl ketone, methylanthranilic acid methyl ester, p-methyl acetophenone, methyl chavicol, p-methylquinoline, methyl beta-naphthyl ketone, methyl-n-nonylacetaldehyde, methyl n-nonyl ketone, muscone, beta-naphthol ethyl ether, beta-naphthol methyl ether, nerol, n-nonylaldehyde, nonyl alcohol, n-octylaldehyde, p-oxyacetophenone, pentadecanolide, beta-phenylethyl alcohol, phenylacetaldehyde dimethyl acetal, phenylacetic acid, pulegone, safrol, salicylic acid isoamyl ester, salicylic acid methyl ester, salicylic acid hexyl ester, salicylic acid cyclohexyl ester, santalol, sandelice, skatole, terpineol, thyme, thymol, Troenan, gamma-undecalactone, vanillin, veratraldehyde, cinnamaldehyde, cinnamyl alcohol, cinnamic acid, cinnamic acid ethyl ester, cinnamic acid benzyl ester, diphenyl oxide, limonene, linalool, linalyl acetate and propionate, Melusat, menthol, menthone, methyl n-heptenone, pinene, phenylacetaldehyde, terpinyl acetate, citral, citronellal and mixtures thereof.

The combination of (a) the selected amino alcohol compound, (b) scent aldehyde and/or scent ketone and (c) the selected silicic acid ester is preferably employed in washing or cleaning agents, fabric softeners or cosmetics. They can be solid, gel-like or liquid formulations, wherein solid formulations can be in the form of powders, granulates, tablets. The liquid formulations can be solutions, emulsions or dispersions. Liquid washing or cleaning agents and fabric softeners preferably comprise water as the major solvent.

The combination of (a) the selected amino alcohol compound, (b) scent aldehyde and/or scent ketone and (c) the selected silicic acid ester is typically employed in end formulations, i.e. ready for use washing or cleaning agents, fabric softeners or cosmetics, in amounts of less than 10 wt %, preferably less than 5 wt %, in particular less than 3 wt %.

The combination of (a) the selected amino alcohol compound, (b) scent aldehyde and/or scent ketone and (c) the selected silicic acid ester is preferably employed in washing or cleaning agents or fabric softeners.

In addition to the combination of (a) the selected amino alcohol compound, (b) scent aldehyde and/or scent ketone and (c) the selected silicic acid ester and the optional additional scents, the washing or cleaning agent or the fabric softener can comprise further ingredients that improve the application-specific and/or esthetic properties of the washing or cleaning agent or the fabric softener. In the context of the present invention, the washing or cleaning agent or the fabric softener preferably additionally comprises one or a plurality of materials from the group of the surfactants, builders, bleaching agents, bleach catalysts, bleach activators, enzymes, electrolytes, non-aqueous solvents, pH adjustors, perfume compositions, perfume carriers, fluorescent agents, dyes, hydrotropes, foam inhibitors, silicone oils, soil-release polymers, graying inhibitors, shrink preventers, anti-crease agents, color transfer inhibitors, additional antimicrobials, germicides, fungicides, antioxidants, preservatives, corrosion inhibitors, antistats, bittering agents, ironing aids, water-repellents and impregnation agents, swelling and non-skid agents, softening components, skin-care agents, booster polymers and UV-absorbers.

Example 1

For the determination of the elimination of malodors a domestic washing machine (Miele W1735) was loaded with 3 kg of worn washing as well as 75 ml of a liquid heavy-duty washing agent that comprised 0.45 wt % perfume (relative to the total liquid washing agent). The washing was washed at 40° C. and then left for 4 days at 20° C. in the washing machine drum (V1). The perfume of the liquid heavy-duty washing agent comprised octanal, cyclamen aldehyde and 2-methylundecanal.

Ten persons trained in olfaction smelled the washing when fresh, after 1 day and after 4 days and measured the intensity of the malodor on a scale of 1 to 10 (1=no longer perceptible to 10=extremely strong). A malodor results from the bacteria present in the washing machine and in the wash water as well as from the contribution from the worn washing.

In another washing test (V2), 0.6 wt % (relative to the total liquid washing agent) of a mixture of silicic acid esters composed of silicic acid phenylethyl ester, silicic acid geranyl ester and silicic acid citronellyl ester were additionally added to the heavy-duty washing agent.

In another washing test (V3), 2 wt % (relative to the total liquid washing agent) of a mixture of amino alcohols composed of 2-amino-1,3-propane diol and 2-amino-2-methyl-1,3-propane diol were additionally added to the heavy-duty washing agent.

In yet another washing test (E1), 0.3 wt % (relative to the total liquid washing agent) of a mixture of silicic acid esters composed of silicic acid phenylethyl ester, silicic acid geranyl ester and silicic acid citronellyl ester and 1 wt % (relative to the total liquid washing agent) of a mixture of amino alcohols composed of 2-amino-1,3-propane diol and 2-amino-2-methyl-1,3-propane diol were additionally added to the heavy-duty washing agent.

The results are presented in Table 1.

TABLE 1

| | Intensity of the malodor | | | |
|---|---|---|---|---|
| | V1 | V2 | V3 | E1 |
| Fresh | 2 | 2.2 | 2.5 | 2.3 |
| 1 day | 5.7 | 4.5 | 3.3 | 2.5 |
| 4 days | 8.1 | 7.4 | 4 | 2.3 |

The results show the significantly improved performance of the combination of (a) a selected amino alcohol compound of the general Formula (I), (b) a scent aldehyde and/or scent ketone and (c) a selected silicic acid ester for the elimination of malodors, in particular over a period of several days.

Example 2

A cotton terrycloth fabric (size: 30×30 cm) was forcibly applied with 100 mg of the malodor "sweat" (20 wt % octanoic acid, 20 wt % nonanoic acid, 20 wt % 3-methylbutanoic acid, 2-ethyl-2-hexenoic acid and 20 wt % 3-mercapto-1-hexanol).

A domestic washing machine (Miele W1735) was then charged with 3.5 kg of accompanying washing as well as the forcibly applied fabric cloths. In addition, 75 ml of a liquid heavy-duty washing agent that comprised 0.45 wt % perfume (relative to the total liquid washing agent) were added.

The washing was washed at 40° C. and then left for 4 days at 20° C. in the washing machine drum (V1). The perfume of the liquid heavy-duty washing agent comprised octanal, cyclamen aldehyde and 2-methylundecanal.

Further washing tests were carried out, in which the washing machine was dosed, in addition to the washing agent, with 0.6 wt % (relative to the total liquid washing agent) of a mixture of silicic acid esters composed of silicic acid phenylethyl ester, silicic acid geranyl ester and silicic acid citronellyl ester (V2), 2 wt % (relative to the total liquid washing agent) of a mixture of amino alcohols composed of 2-amino-1,3-propane diol and 2-amino-2-methyl-1,3-propane diol (V3) and 0.3 wt % (relative to the total liquid washing agent) of a mixture of silicic acid esters composed of silicic acid phenylethyl ester, silicic acid geranyl ester and silicic acid citronellyl ester and 1 wt % (relative to the total liquid washing agent) of a mixture of amino alcohols composed of 2-amino-1,3-propane diol and 2-amino-2-methyl-1,3-propane diol (E1).

The results are presented in Table 2.

TABLE 2

| | Intensity of the malodor | | | |
|---|---|---|---|---|
| | V1 | V2 | V3 | E1 |
| Fresh | 9 | 8.6 | 5.7 | 5 |
| 1 day | 7.4 | 7.1 | 3.3 | 2.5 |
| 4 days | 6.8 | 6.4 | 2.9 | 2.3 |

The results show the significantly improved performance of the inventive combination of the combination of (a) a selected amino alcohol compound of the general Formula (I), (b) a scent aldehyde and/or scent ketone and (c) a selected silicic acid ester for the elimination of malodors, in particular the malodor "sweat", in particular over a period of several days.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A composition for providing the delayed release of scent comprising:

(a) an amino alcohol compound of the general Formula (I)

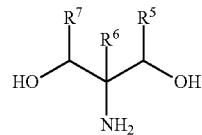

(I)

wherein $R^5$, $R^6$, $R^7$ independently of each other stand for H or a hydrocarbon group that can be acyclic or cyclic, substituted or unsubstituted, branched or unbranched as well as saturated or unsaturated, or mixtures of these compounds, (b) a scent aldehyde and/or scent ketone and (c) a silicic acid ester of the general Formula (II):

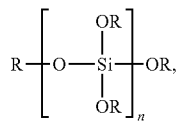

(II)

wherein all R, independently of each other, are selected from the group that comprises H, the linear or branched, saturated or unsaturated, substituted or unsubstituted $C_{1-6}$ hydrocarbon groups and scent alcohol residues, and n assumes values in the range 2 to 100, wherein the silicic acid ester at least partially comprises scent alcohol residues.

2. The composition according to claim 1, wherein the scent aldehyde and/or the scent ketone reacts at least partially under cyclization with the amino alcohol compound of the general Formula (I) to form a 1-aza-3,7-dioxabicyclo [3.3.0]octane compound of the general Formula (III)

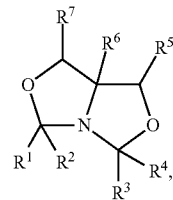

(III)

wherein $R^1$, $R^2$, $R^3$, $R^4$ independently of each other stand for residues that in a compound of the general Formula $R^1$—C(=O)—$R^2$ or $R^3$—C(=O)—$R^4$ form a scent aldehyde containing at least 6 carbon atoms or a scent ketone containing at least 6 carbon atoms.

3. The composition according to claim 2, wherein $R^2$, $R^4$, $R^5$, $R^6$, $R^7$ mean hydrogen and $R^1$ and $R^3$ each mean a $C_{5-24}$ hydrocarbon residue.

4. The composition according to claim 1, wherein the scent aldehyde and the scent ketone are selected from the jasmones, ionones, damascones and damascenones, menthone, carvone, iso-E-super, methylheptenone, melonal, cymal, ethyl vanillin, helional, hydroxycitronellal, koavone, methylnonylacetaldehyde, phenylacetaldehyde, undecylenaldehyde, 3-dodecen-1-al, alpha-n-amylcinnamaldehyde, benzaldehyde, 3-(4-tert-butylphenyl)-propanal, 2-methyl-3-(para-methoxyphenylpropanal), 2-methyl-4-(2,6,6-trimethyl-2(1)-cyclohexen-1-yl)butanal, 3-phenyl-2-propenal, cis/trans-3,7-dimethyl-2,6-octadien-1-al, 3,7-dimethyl-6-octen-1-al, [(3,7-dimethyl-6-octenyl)oxy]acetaldehyde, 4-isopropylbenzyaldehyde, 2,4-dimethyl-3-cyclohexene-1-carboxyaldehyde, 2-methyl-3-(isopropylphenyl)propanal, decylaldehyde, 2,6-dimethyl-5-heptenal, alpha-n-hexylcinnamaldehyde, 7-hydroxy-3,7-dimethyloctanal, undecenal, 2,4,6-trimethyl-3-cyclohexene-1-carboxaldehyde, 1-dodecanal, 2,4-dimethylcyclohexene-3-carboxaldehyde, 4-(4-hydroxy-4-methylpentyl)-3-cylohexene-1-carboxaldehyd, 2-methylundecanal, 2-methyldecanal, 1-nonanal, 1-octanal, 2,6,10-trimethyl-5,9-undecadienal, 2-methyl-3-(4-tert-butyl)propanal, dihydrocinnamaldehyde, 3,7-dimethyloctan-1-al, 1-undecanal, 10-undecen-1-al, 4-hydroxy-3-methoxybenzaldehyde, trans-4-decenal, 2,6-nonadienal, para-tolylacetaldehyde, 3,7-dimethyl-2-methylene-6-octenal, 2-methyloctanal, alpha-methyl-4-(1-methylethyl)benzeneacetaldehyde, 2-methyl-3-phenyl-2-propen-1-al, 3,5,5-trimethylhexanal, 3-propyl-bicyclo[2.2.1]hept-5-ene-2-carbaldehyde, 9-decenal, 3-methyl-5-phenyl-1-pentanal, methylnonylacetaldehyde, citral, 1-decanal, florhydral, 2,4-dimethyl-3-cyclohexene-1-carboxaldehyde, heliotropin and mixtures thereof.

5. The composition according to claim 1, wherein the scent aldehyde and/or the scent ketone reacts at least partially under cyclization with the amino alcohol compound of the general Formula (I) to form a compound of the general Formula (IV)

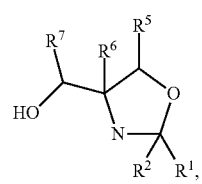

(IV)

wherein $R^1$ and $R^2$, independently of one another stand for groups that in a compound of the general Formula $R^1$—C(=O)—$R^2$ form a scent aldehyde containing at least 6 carbon atoms or a scent ketone containing at least 6 carbon atoms.

6. The composition according to claim 1, wherein at least 5 mol % of the R residues of the general Formula (II) are selected from the group methyl, ethyl, n-propyl, isopropyl, n-butyl, isobutyl and tert-butyl.

7. The composition according to claim 1, wherein at least 10 mol %, of the R residues of the general Formula (II) are selected from the group consisting of the residues of the scent alcohols 10-undecen-1-ol, 2,6-dimethylheptan-2-ol, 2-methylbutanol, 2-methylpentanol, 2-phenoxyethanol, 2-phenylpropanol, 2-tert-butylcyclohexanol, 3,5,5-trimethylcyclohexanol, 3-hexanol, 3-methyl-5-phenylpentanol, 3-octanol, 3-phenylpropanol, 4-heptenol, 4-isopropylcyclohexanol, 4-tert-butylcyclohexanol, 6,8-dimethyl-2-nonanol, 6-nonen-1-ol, 9-decen-1-ol, alpha-methylbenzyl alcohol, alpha-terpineol, amyl salicylate, benzyl alcohol, benzyl salicylate, beta-terpineol, butyl salicylate, citronellol, cyclohexyl salicylate, decanol, dihydromyrcenol, dimethylbenzyl carbinol, dimethylheptanol, dimethyloctanol, ethyl salicylate, ethyl vanillin, eugenol, farnesol, geraniol, heptanol, hexyl salicylate, isoborneol, isoeugenol, isopulegol, linalool, menthol, myrtenol, n-hexanol, nerol, nonanol, octanol, p-menthan-7-ol, phenylethyl alcohol, phenol, phenyl salicylate, tetrahydrogeraniol, tetrahydrolinalool, thymol, trans-2-cis-6-nonadienol, trans-2-nonen-1-ol, trans-2-octenol, undecanol, vanillin, cinnamyl alcohol and mixtures thereof.

8. The composition according to claim 1, wherein n assumes values in the range 2 to 50.

9. A washing or cleaning agent, fabric softener or cosmetics, comprising:

(a) an amino alcohol compound of the general Formula (I)

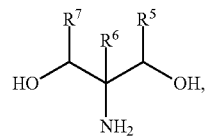

wherein $R^5$, $R^6$, $R^7$ independently of each other stand for H or a hydrocarbon group that can be acyclic or cyclic, substituted or unsubstituted, branched or unbranched as well as saturated or unsaturated, or mixtures of these compounds, (b) a scent aldehyde and/or scent ketone and (c) a silicic acid ester of the general Formula (II):

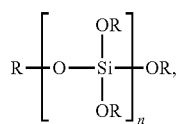

wherein all R, independently of each other, are selected from the group that comprises H, the linear or branched, saturated or unsaturated, substituted or unsubstituted $C_{1-6}$ hydrocarbon groups and scent alcohol residues, wherein the silicic acid ester at least partially comprises scent alcohol residues, and n assumes values in the range 2 to 100.

10. A method for extending the perceived scent of washing or cleaning agents, fabric softeners or cosmetics or of hard surfaces treated with them, wherein the composition according to claim 1 is added to the washing or cleaning agents, fabric softeners or cosmetics, and wherein the scent is released by hydrolysis.

11. A method for eliminating malodors of worn washing comprising the step of contacting the worn washing with a composition comprising:

(a) an amino alcohol compound of the general Formula (I)

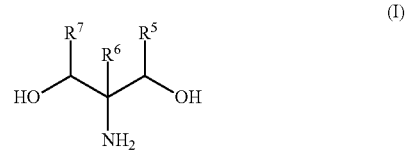

wherein $R^5$, $R^6$, $R^7$ independently of each other stand for H or a hydrocarbon group that can be acyclic or cyclic, substituted or unsubstituted, branched or unbranched as well as saturated or unsaturated, or mixtures of these compounds, (b) a scent aldehyde and/or scent ketone and (c) a silicic acid ester of the general Formula (II):

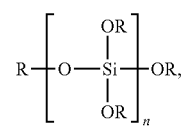

wherein all R, independently of each other, are selected from the group that comprises H, the linear or branched, saturated or unsaturated, substituted or unsubstituted $C_{1-6}$ hydrocarbon groups and scent alcohol residues, wherein the silicic acid ester at least partially comprises scent alcohol residues, and n assumes values in the range 2 to 100.

* * * * *